(12) United States Patent
Wyss

(10) Patent No.: US 8,684,991 B2
(45) Date of Patent: Apr. 1, 2014

(54) FLEXIBLE CONTAINER WITH INSERT PART

(75) Inventor: Martin Wyss, Burgdorf (CH)

(73) Assignee: Roche Diagnostics International AG, Rotkreuz (CH)

( * ) Notice: Subject to any disclaimer, the term of this patent is extended or adjusted under 35 U.S.C. 154(b) by 0 days.

(21) Appl. No.: 13/232,477

(22) Filed: Sep. 14, 2011

(65) Prior Publication Data

US 2012/0238955 A1     Sep. 20, 2012

Related U.S. Application Data

(63) Continuation of application No. PCT/EP2010/000672, filed on Feb. 4, 2010.

(30) Foreign Application Priority Data

Mar. 16, 2009 (EP) .................................... 09155279

(51) Int. Cl.
*A61B 19/00* (2006.01)

(52) U.S. Cl.
USPC ........................................................ 604/410

(58) Field of Classification Search
USPC ............ 604/80, 251, 262, 151–153, 408, 410
See application file for complete search history.

(56) References Cited

U.S. PATENT DOCUMENTS

| | | | |
|---|---|---|---|
| 4,632,673 A | | 12/1986 | Tiitola et al. |
| 4,723,956 A | * | 2/1988 | Schnell et al. ................ 604/414 |
| 5,030,203 A | | 7/1991 | Wolf, Jr. et al. |
| 5,391,163 A | * | 2/1995 | Christine et al. .............. 604/408 |
| 5,478,211 A | * | 12/1995 | Dominiak et al. ............ 417/234 |
| 6,179,823 B1 | | 1/2001 | Niedospial, Jr. |
| 7,025,754 B2 | * | 4/2006 | Proicou et al. ................ 604/408 |
| 2004/0001655 A1 | | 1/2004 | Proicou et al. |
| 2006/0184119 A1 | | 8/2006 | Remde et al. |
| 2007/0049865 A1 | | 3/2007 | Radmer et al. |
| 2007/0123820 A1 | | 5/2007 | Gafner-Geiser et al. |

FOREIGN PATENT DOCUMENTS

| | | |
|---|---|---|
| CN | 2088430 U | 11/1991 |
| CN | 1929807 A | 3/2007 |
| EP | 2 179 755 A1 | 10/2008 |
| EP | 2 193 815 A1 | 6/2010 |
| WO | 2004/009162 A1 | 1/2004 |
| WO | 2008/122135 A1 | 10/2008 |

* cited by examiner

*Primary Examiner* — Nicholas Lucchesi
*Assistant Examiner* — Melissa A Snyder
(74) *Attorney, Agent, or Firm* — Dinsmore & Shohl LLP

(57) ABSTRACT

A flexible container for storing a liquid medicament comprises a container wall consisting of two wall sheets of flexible material that are sealed together is disclosed. The container may comprise a storage compartment for the liquid medicament, and an access opening on one of the wall sheets. The storage compartment and the access opening may be in fluid connection. The access opening is designed to be fluidly connected to an outer conduit system. An insert part may be arranged between the two wall sheets with positive locking, and may fluidly connect the storage compartment and the access opening.

14 Claims, 10 Drawing Sheets

(a)

(b)

(a)

(b)

(c)

(d)

(a)

(b)

(c)

(a)

(b)

(c)

FLEXIBLE CONTAINER WITH INSERT PART

CROSS REFERENCE TO RELATED APPLICATIONS

This application is a continuation of International Application No. PCT/EP2010/000672 filed Feb. 4, 2010, which claims priority to European Patent Application No. EP09155279.4 filed on Mar. 16, 2009.

TECHNICAL FIELD

The disclosed embodiments of the invention relate to a flexible container for storing a liquid medicament to be administered to a patient by an infusion pump device, an insert part for use with such a flexible container, and a device for the automated release of a liquid medicament, comprising, incorporating, and/or capable of using such a flexible container.

BACKGROUND

Devices for the automated release of liquid medicaments are normally used with patients who have a continuous and, in the course of the day, a varying need of a medicine which can be administered by subcutaneous infusion. Specific applications are, for example, certain pain therapies and the treatment of diabetes, in which computer controlled infusion pump devices, such as insulin pumps, are used. Such devices can be carried by a patient on the body, and can contain a certain amount of liquid medicament in a medicine reservoir in the form of a container. The medicine reservoir often comprises medicine sufficient for one or more days. The liquid medicament is supplied to the patient's body from the medicine reservoir through an infusion cannula or an injection needle.

Particularly in self-administration of medicaments, for example insulin, the patients that are using the medicament in question and administering it themselves by means of an infusion pump, are increasingly emphasizing convenience and discretion. As a consequence the dimensions of such infusion devices are limited, and in particular the overall length, width and thickness should be as small as possible, in order not be evident through clothing and to be carried comfortably as possible.

While there are fully or partly disposable single-use infusion pump devices, such devices are typically non-disposable and are loaded with a disposable drug cartridge. Disposable cartridges are preferable for sterility and contamination prevention reasons. They may be delivered either pre-filled with a certain liquid medicament, or empty, ready to be filled by a user. Said self-filling of containers has the advantage that also medicaments that are not readily available in pre-filled containers can be used for such infusion pump devices, thereby providing the patient with a larger choice of sources for his medicaments. Furthermore the stability of many medicaments in liquid form, particularly in plastic containers, can only be guaranteed by the manufacturer for a number of days.

The standard infusion pump devices that are carried on or near the body have a medicine reservoir with a cylindrical ampoule and a displacement piston, which is pushed into the ampoule by a piston rod or a threaded spindle in order to convey the liquid medicament. These known designs have the disadvantage of being longer and/or thicker than desired, with the resulting dimensions being detrimental to the provision of compact infusion pumps.

Manufacturers try to meet the demand of small infusion pump devices by various means. For example, the infusion pump can be divided into structural assemblies which are each arranged in their own, smaller, housings and can be joined to one another by wireless or wired connection. An example of such a modular infusion pump device is disclosed in US 2006/0184119 A1.

Another possibility is the use of containers of particularly flat construction. For example, a cylindrical ampoule may be replaced by a container with a rectangular or another suitable cross-section, and which interacts with a displacement piston of a corresponding shape. Different embodiments of such compact medicine reservoir devices are shown in WO 2008/122135 A1.

A further approach to reduce the overall volume of an infusion pump device is to replace the syringe-type dosing mechanism, in which a piston is displaced along a long container axis, by an actuator, thereby conveying the appropriate amount of liquid medicine by a downstream pump system. In such a device, a miniaturized pump is arranged downstream of the reservoir, and causes a suction pressure that conveys the product from the reservoir to its destination. An example for such a pump is WO 2004/009162 A1.

For some of such infusion pump devices, the suction pressure achievable with such a pump system is not very high. A suitable container for such devices is disclosed in US 2007/0123820 A1, comprising a flat container and a flat piston body arranged in the body in a sliding manner. When fully filled, such a container has a ratio between its maximum height and its overall width of less than 1.25. The cross-section area of the container in relation to the displacement axis is much larger than for conventional cylinder-piston arrangements, and already a comparably small pressure gradient as generated by a miniaturized pump is able to overcome the friction force of the piston sealing gliding on the inner container wall.

In another approach the rigid container and movable piston are replaced by a flexible container. Such a flexible container may, for example, have the form of two flexible wall sheets that are sealed together. Flexible containers have the advantage of a smaller volume surplus of the container in relation to its content, which reduces the manufacture costs and the achievable dimensions of an infusion pump device using such a flexible container. The volume of a flexible container for use in an infusion pump device may be up to 10 ml, for example. A typical range for diabetes therapy is 1.5 to 3.5 ml. For other therapies, e.g. pain therapies, which require other administration regimes, other volume ranges may be more preferable.

For use in an infusion pump device, the flexible container must be connected to a conduit system of the device. For that purpose, the flexible container may be provided with a port. Such a port can be mounted on the container with a flange sealed to a container wall sheet. US 2007/0049865 A1 discloses such a container. The port is provided with a septum, which is to be punctured by a hollow needle of the conduit system of the infusion pump device. Another possibility used for flexible containers are ports in the form of either flexible tubes or rigid connection pieces that are welded between the two sheets of the container at the periphery of the flexible container. The fastening of the port to the container, for example by gluing or welding, requires a precise production control to avoid high rejection rates, and which furthermore limits the choice of suitable materials.

A common problem of flexible containers with ports as used, for example, in IV bags, is the dead volume resulting between the collapsed container and the port. Said dead volume cannot be used, meaning that it cannot be emptied. Thus a complete drainage of the contents of a flexible container is not possible. The resulting loss of useable container volume due to the dead volume is particularly high for smaller containers, which are suitable for infusion pumps, with a total volume of only 5 ml or less. In standard liquid medicament containers for infusion pump devices, the dead volume may lie in the range of at least 5% of the overall volume. For single-use container filled with the medicament, the dead volume considerably increases the effective costs per dose and thus of the overall therapy costs, since a certain percentage of the medicament will inevitably remain in the container and has to be disposed. This cost effect is particularly important for expensive medicaments. In addition to the increased costs, the dead volume leads also to an increase of the overall volume of the flexible container, and thus of the infusion pump device with such a flexible container.

A further problem, particularly of flexible containers as they are known, is air remaining in the container. If, for example, a flexible container is provided empty, which is intended to be filled with the appropriate medicament by the user himself, the dead volume is initially filled with air. However, removing the air from flexible containers as they are known from the state of the art will require a certain skill of a user. If said air remains in the container or in the fluidic system of a pump system, air bubbles may be administered instead of the liquid medicament, which leads to potentially dangerous dosing errors. Furthermore, the administration of air into a patient's body should generally be avoided for medical reasons.

Yet another problem of air in the fluidic system is the reduced stiffness of the fluidic system. Due to the high compressibility of gases such as air in relation to liquids such as water, it becomes difficult to measure the exact pressure in the fluidic system. This impedes the detection of blockages or occlusions in the fluidic system of an infusion pump device by measuring the fluidic pressure.

SUMMARY

A flexible container for storing a liquid medicament and connection to an outer conduit system is disclosed. The flexible container may comprise a container wall consisting of two wall sheets of flexible material that are sealed; a storage compartment for the liquid medicament; an access opening on one of the wall sheets, wherein the storage compartment and the access opening are in fluid connection, and the access opening is designed to be fluidly connected to the outer conduit system; and an insert part that is arranged between the two wall sheets with positive locking, and that fluidly connects the storage compartment and the access opening.

BRIEF DESCRIPTION OF THE DRAWINGS

FIGS. 5(a), 5(b) and 5(c) schematically show yet another embodiment of an insert part according to the invention, in a side view, in a cross-section through plane b-b, and in a top view, respectively, while FIG. 5(d) shows the access area of a container according to the invention with such an insert part.

Figure 1:
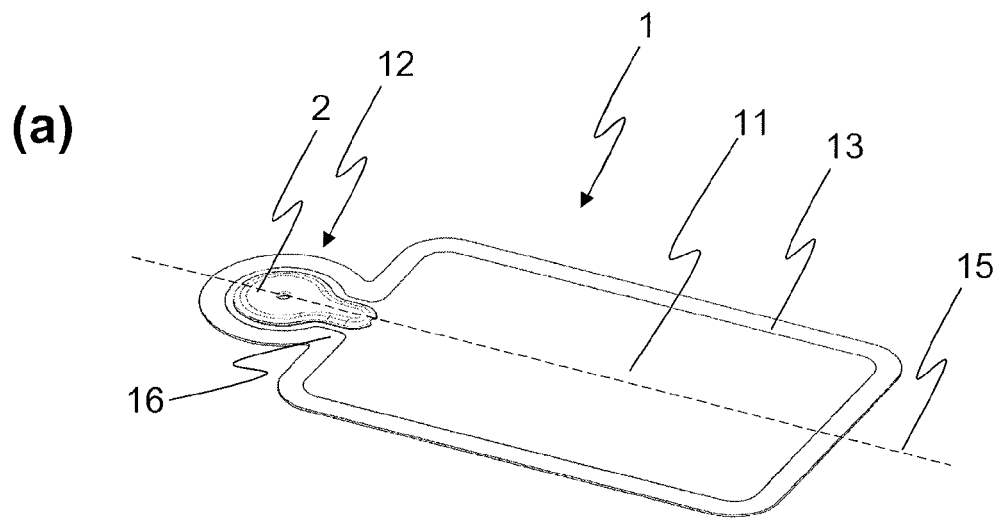
FIGS. 1(a) and 1(b) schematically show an embodiment of a flexible container according to the invention in a perspective view, and in an explosion view, respectively.
Figure 1:
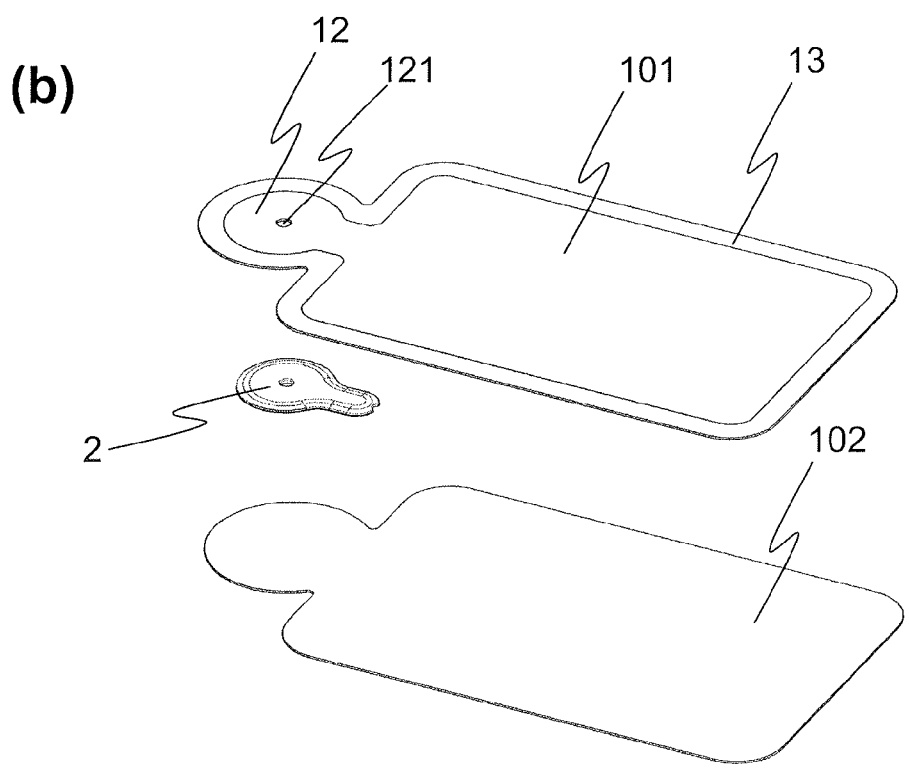

LIST OF REFERENCE NUMERALS 1 flexible container
101, 102 wall sheet
103 circular hole
11 storage volume
12 access area
121 access opening
13 sealing rim
14 sealed area
15 longitudinal axis
16 neck, constriction
17 positioning element
2 insert part
21 body of insert part
211 upper surface
212 lower surface
22 drain channel
221 drain channel network
222 protrusion
23 inner conduit
24 needle stop
25 positioning element
26 distance element
27 sealing lip
28 secondary sealing lip
3 connection device
31 lower clamp part
32 upper clamp part
33, 33' conduit system
331 septum
332 hollow needle
34 sealing element
35 pressure element

DETAILED DESCRIPTION

Various embodiments of the invention provide a flexible container for storing a liquid medicament to be administered to a patient, which does not comprise the disadvantages of the known containers. Particularly a flexible container according to an embodiment of the invention may be easily connected to a device for the automated release of a liquid medicament. Furthermore a flexible container according to an embodiment the invention may have a reduced dead volume, and may be easily connected to a device for the automated release of a liquid medicament. For example, for flexible containers according to an embodiment of the invention, the remaining dead volume lies in a range of 1 to 2% or less. It may also have dimensions that are suitable for being carried on or near the body.

In addition a flexible container according to an embodiment of the invention may be producible with high quality at low costs, and may comprise a minimum number of components.

Various embodiments of the invention provide advantageous insert parts for use in such flexible containers and for fluidly connecting a flexible container with a connection device such that the flexible container can be connected with a device for the automated release of a liquid medicament.

Yet other embodiments of the invention provide a device for the automated release of a liquid medicament comprising, incorporating, and/or capable of using such a flexible container.

In one embodiment, a flexible container for storing a liquid medicament comprises a container wall consisting of two wall sheets of flexible material that are sealed together. The container comprises a storage compartment for the liquid medicament, and an access opening on one of the wall sheets. The storage compartment and the access opening are in fluid connection, and the access opening is designed to be fluidly connected to an outer conduit system. An insert part is arranged between the two wall sheets with positive locking, and fluidly connects the storage compartment and the access opening.

The access opening of the flexible container is intended to be fluidly connected to an outer conduit system of an infusion pump device either directly or using a suitable connection device.

The positive locking is achieved by the interaction of elements of the insert part with elements of the wall sheets. For example, the periphery of the insert part may be positively locked between the two adjacent wall sheets and the sealing rim of the wall sheets. In such a case, the direction of the locking force is essentially parallel to the wall sheets. The insert part may have some play parallel to the wall sheets, as long as the fluid connection between the storage compartment and the access opening via the insert part is given.

In an embodiment of a flexible container, the insert part is arranged and positively locked in a distinct access area of the container. Preferably said access area is separated from the storage compartment by a neck or constriction.

In another embodiment of a flexible container, elements are provided for positioning and/or fixating the flexible container in a connection device, and particularly in a connection device of an infusion pump device.

Preferably said elements for positioning and/or fixating are two or more holes and/or grooves and/or protrusions arranged in a sealed area of the container, and/or in an area of the wall sheets outside of the sealed area that does not belong to the storage compartment.

In yet another embodiment of a flexible container, the access opening comprises a hole arranged in a wall sheet adjacent to the insert part, preferably above an opening of a conduit system of the insert part. The access opening may, for example, have a diameter of about 1.5 mm or less. In said embodiment of the flexible container the insert part may comprise a sealing lip arranged on the upper surface of the insert part, wherein the sealing lip protrudes through the hole of the access opening.

In a variant of said embodiment of the flexible container, the positive locking of the insert part in the flexible container is at least partially achieved by the sealing lip protruding through the hole of the access opening.

A flexible container according to an embodiment may preferably include a connection device for use in an infusion pump device, comprising two clamp parts that are adapted to positively and/or non-positively locking the flexible container, and to fluidly connecting an access opening of the flexible container to a conduit system of the connection device. Typically, in such a variant of a flexible container the access opening is not directly accessible. Preferably the flexible container and the connection device are provided as a compact pre-assembled unit.

In an embodiment of such a flexible container the clamp part facing toward the access opening comprises a sealing element that is adapted to fluidly connecting the conduit system with the access opening of the flexible container.

In another embodiment of such a flexible container the surface of the clamp parts of the connection device is adapted to the exterior shape of the flexible container, particularly to the exterior shape of an access area of the container.

Additionally or alternatively one or both clamp parts may also comprise resilient elements directed towards the opposite clamp part, in order to increase the friction-lock of the container or to improve the sealing.

The connection device may comprise further functional elements such as, for example, a bubble trap, a pressure sensor, or a pressure transfer membrane for coupling a conduit system of the connection device to a pressure sensor. It may also comprise a pumping/dosing mechanism, or part of a pumping mechanism, such as a micro membrane pump, or a micro plunger pump.

In one embodiment of a container, the container comprises a bubble trap. Said bubble trap may be an integral part of the container, fully or in part. More preferably it may comprise a bubble trap as it is disclosed in the European patent application No. 09155216.6 with the title "Bubble trap system for an infusion pump device", filed by the applicants on the same day as the present application.

The connection device may also comprise further functional elements, e.g. a septum, a degassing membrane, a pressure sensor, a pressure transfer membrane, a pump chamber and/or a pumping mechanism, complete or in part. The connection device may also be realized as an integral part of a flexible container, permanently mounted on said flexible container, or as an integral part of an infusion pump device.

In an embodiment of a flexible container comprising a connection device, said connection device comprises elements for positioning and/or fixating the flexible container, for example positioning bolts, preferably interacting with elements for positioning and/or fixating of the flexible container.

Another embodiment of a flexible container comprises an insert part according to the invention, as they will be described further below.

In addition, a flexible container according to another embodiment may be provided with one or more additional ports mounted to the container wall, in addition to the access area. These additional ports may be used for transferring liquid to and from the storage compartment of the container, or may be used to deaerate the container if needed. Particularly a container according to an embodiment of the invention can comprise one or more ports as disclosed in European Patent Application No. 08167548 of the applicants, which is hereby incorporated by reference as part of this disclosure in its entirety. A flexible container according to an embodiment of the invention can also have the structural elements of a flexible container as disclosed in said application.

Furthermore a flexible container according to an embodiment of the invention may comprise additional preformed drain channels, formed by the two wall sheets. European Patent Application No. 08170627 of the applicants discloses a number of possible variants of such drain channels. The access area and the storage compartment of the container, for example, may be connected by one or more such additional drain channels. The content of said application is hereby incorporated by reference as part of this disclosure in its entirety.

Since essentially all elements necessary for fluidly connecting the flexible container to an infusion pump device are arranged inside the container, and no bulky external port is required, the overall volume of a container according to an embodiment of the invention and thus of an infusion pump device with such a container is considerably reduced. At the same time the dead volume is kept at a minimum.

Typically a flexible container according to an embodiment of the invention will be provided hermetically closed and sealed, to keep the inside of the container sterile. The container will either be completely or partially filled with a liquid medicament, or will be empty.

An insert part according to an embodiment of the invention for use in a flexible container according to an embodiment of the invention comprises an essentially flat body with a first, upper surface and a second, lower surface, and an inner conduit opening toward the upper surface. The inner conduit is fluidly connected to one or more drain channels and/or a drain channel network that lead to an outer edge of the insert part body.

In an embodiment of an insert part, the one or more drain channels are embodied as depressions arranged on the lower surface, and/or as tubular conduits arranged inside the body of the insert part.

In another embodiment of an insert part, one or more positioning elements are provided that are adapted to positively lock the insert part in the flexible container.

In yet another embodiment of an insert part, a sealing lip is arranged on the upper surface, for sealingly connecting the inner with an external conduit system. The sealing lip preferably consists of a material with higher elasticity than the material of the body of the insert part. Alternatively the sealing lip may consist of the same material as the body of the insert part. In any case the elasticity of the sealing lip should be higher that the elasticity of the counterpart of the connection device interacting with the sealing lip.

In a further embodiment of an insert part, the insert part comprises a secondary sealing lip arranged on the upper surface, for sealingly connecting the upper surface with an adjacent wall sheet of the flexible container.

An insert part according to an embodiment of the invention may also comprise a septum, arranged in the inner conduit.

When mounted in a flexible container, the essentially flat upper surface of the insert part according to an embodiment of the invention lies adjacent to the wall sheet. The inner conduit, leading to the flat upper surface of the insert part, opens to the access opening in the wall sheet.

The insert part is arranged within a flexible container according to an embodiment of the invention with positive locking, and thus does not have to be mechanically attached to the wall sheets. Thus such a container can consist of only three parts, of which only two, namely the wall sheets, have to be sealingly connected, along a peripheral sealing rim. When one single, folded sheet is used instead of two separate wall sheets, even only two parts are sufficient for a container according to the invention. This noncomplex design of a flexible container according to an embodiment of the invention simplifies the assembly of the container, and consequently reduces manufacturing costs. Furthermore, since the insert part does not have to be directly attached to the wall sheets of the container, it is not necessary to choose materials for the insert part and the adjacent layer of the wall that are compatible for being sealed together, which provides more flexibility for the manufacturer when selecting the most appropriate materials for a certain purpose.

A flexible container according an embodiment of the invention may be connected with an infusion pump device by a suitable connection device. Said connection device interacts with a specific access area of the container, in which the insert part is arranged. Sealing elements of the connection device and/or the insert part provide a liquid-tight connection between a conduit system of the connection device and the access opening of the container.

After a liquid-tight sealing has been established, the storage compartment of the container is finally fluidly connected to the conduit system of the connection device, via the drain channel network and the inner conduit of the insert part. The infusion pump device can now draw the liquid medicament from the container. When the pump device of an infusion pump, arranged downstream of the conduit system of the connection device, sucks liquid, the liquid medicament in the container flows from the storage compartment through the drain channel network and the inner conduit of the insert part to the access opening, and then via the conduit system to the pump device. The container, fully or partially filled in the beginning, will continuously collapse, until finally the two wall sheets abut to each other. It is also possible to fill or refill the flexible container via the connection device.

An advantageous device for the automated release of a liquid medicament, particularly an infusion pump device, comprises, incorporates or is capable of using a flexible container according to the various embodiments of the invention.

As used herein, the terms "medicament" and "liquid medicament" are meant to encompass any drug-containing flowable medicine, or therapeutic or diagnostic liquid, capable of being passed through a delivery element such as a hollow needle in a controlled manner, such as a liquid, solution, gel or fine suspension. Representative drugs include pharmaceuticals such as peptides, proteins, and hormones, biologically derived or active agents, hormonal and gene based agents, nutritional formulas and other substances in both solid (dispensed) or liquid form. In particular the term medicament encompasses insulin preparations ready for administration.

The terms "subcutaneous infusion" and "subcutaneous injection" are meant to encompass any method in which a needle device is inserted at a selected site within the body of a patient for subcutaneous, intravenous, intramuscular or intradermal delivery of a liquid medicament to a subject. Further, the term needle defines a piercing member (including an array of micro needles) adapted to be introduced into or through the skin of a subject.

The terms "drain channel" and "drain channel network" are meant to encompass any arrangement of depressions and protrusions on a surface that provide sufficient interconnected space between the surface and a flexible sheet firmly abutted to said surface that a fluid can flow through said space.

In order to facilitate a fuller understanding of illustrated embodiments of the present invention, reference is now made to the appended drawings. These references should not be construed as limiting the present invention, but are intended to be exemplary only.

One possible embodiment of a flexible container 1 according to the invention is shown in FIG. 1(a) in a perspective view, and also in FIG. 1(b) in an explosion view. The flexible container 1 basically consists of two wall sheets 101, 102 of flexible, liquid-tight material, sealed along a circumferential sealing rim 13, and an insert part 2, arranged between the two wall sheets 101, 102. The insert part 2 is shown in more detail in FIGS. 2(a) and 2(b).

In FIG. 1(a) the container 1 is shown in an empty, fully drained state. The shown container essentially comprises two distinct compartments divided by a neck 16, namely a storage compartment 11 in which the liquid content is stored, and an access area 12, which is essentially filled by the insert part 2. The shape of the access area 12 and the neck 16 are adapted to the shape of the insert part 2, in order to positively locking the insert part 2 within the container 1, and to reduce the dead volume in the access area to a minimum. The periphery of the insert part 2 is positively locked between the two adjacent wall sheets 101, 102 and the sealing rim 13 of the wall sheets. The direction of the locking force is essentially parallel to the wall sheets 101, 102. By appropriately adjusting the manufacturing process, it is possible to obtain a perfect fit of the insert part 2 within the container 1. However, the insert part 2 may also have some play parallel to the wall sheets 101, 102, as long as the fluid connection between the storage compartment 11 and the access opening 121 (FIG. 1(b)) via the insert part 2 is given.

Figure 2:
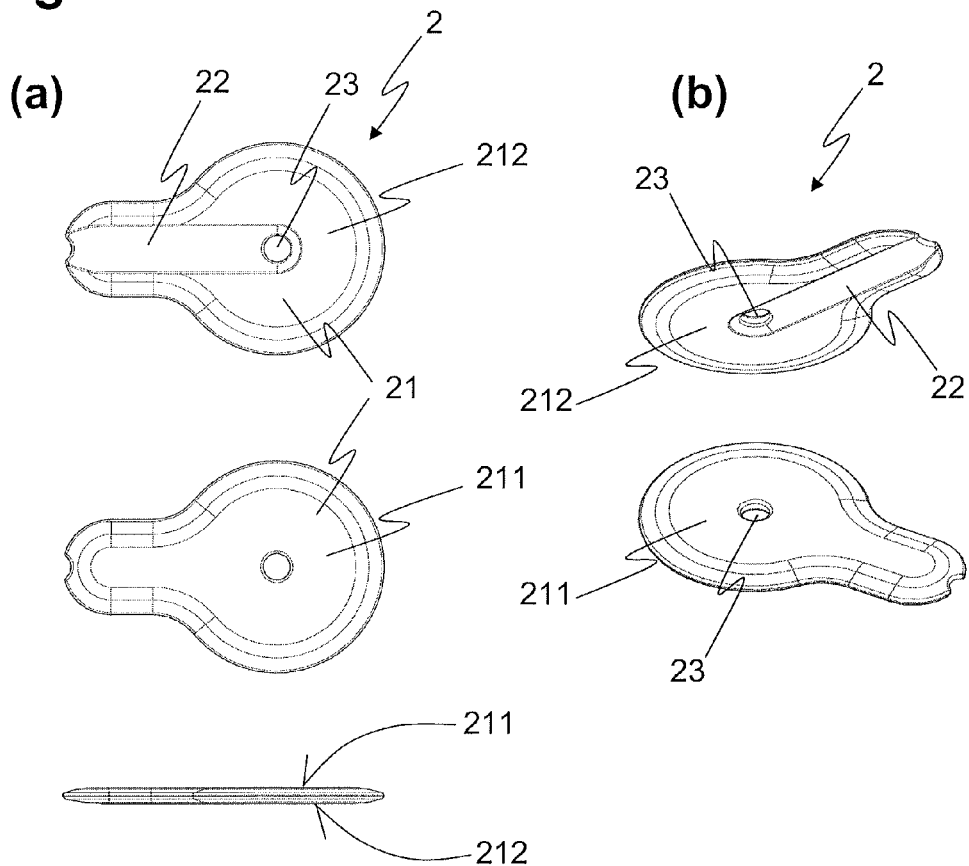
FIG. 2(a) schematically shows the insert part according to the invention as shown in FIG. 1, with a view of the lower and upper surface, and in a side view.
FIG. 2(b) schematically shows the insert part according to the invention as shown in FIG. 1, in a perspective view of the lower and upper surface of FIG. 2(a).

Referring to FIGS. 2(a) and 2(b), the embodiment of the insert part 2 has a flat, drop-like shape with a central circular body part and a tongue part. The rim of the insert part 2 is beveled, in order to minimize the dead volume between the sealing rim 13 and the insert part 2, and to avoid mechanical stress on the preferably thin wall sheets 101, 102. The insert part 2 has an essentially flat upper surface 211, and lower surface 212. A single drain channel 22 is arranged on the lower surface 212 of the insert part, connected to the upper surface 211 by an inner conduit 23, realized as a bore arranged in the center of the insert part 2. The drain channel 22 is realized as an oblong depression on the lower surface 212, leading from the central inner conduit 23 to the end of the tongue part, opening to the storage compartment 11 (FIG. 1(a)). The volume of the drain channel 22 and the inner conduit 23 is much smaller than the total volume of the container, and thus its contribution to the dead volume of the container is negligible.

The sealing of the two wall sheets 101, 102 may be achieved by heat sealing, ultrasonic welding, high-frequency inductive welding, gluing, or any other suitable method for producing flexible containers from sheet-like material that is known to the skilled person. The sheet-like material may be a single foil of a suitable polymer, or a compound foil. The base area of a flexible container according to the invention may have any suitable shape, particularly square, rectangular, circular, oval, hexagonal shape. The shape may also be specially adapted to a specific infusion pump device. Instead of sealing together two separate wall sheets 101, 102, the walls of the container 1 may also be produced from a single sheet that is folded along an axis, and is sealed along the remaining edges. Another possibility known from the state of the art is the use of continuous film tubes for producing the containers.

The material of the wall sheets 101, 102 can be a monolayer film or a multi-layer structure. The wall sheets 101, 102 may consist of one or more polymers of the following families: Polypropylene (PP), Polyethylene (PE), and copolymers; Ethylene Vinyl Acetate (EVA), Polyvinyl Chloride (PVC), Polyvinylidene Chloride (PVDC), Polystyrene (PS), Ethylene Vinyl Alcohol (EVOH), Polyethylene Terephthalate (PET), Polyamide (PA), Polychlorotrifluoroethylene (PCTFE), Cyclic Olefin Copolymer (COC), Thermoplastic Elastomer (TPE), or generally any other polymer material which is known to the skilled person to be suitable for that purpose. The wall sheets 101, 102 may be manufactured, for example, by extrusion, blown film extrusion, coextrusion or lamination. When producing a multilayer structure it may be necessary to include one or more tie layers, or to apply one or more adhesive layers between the functional layers. To improve barrier properties one may also use metalized film, or a silicon oxide or aluminum oxide coating may be applied.

The insert part 2 may consist of any suitable rigid or semi-rigid material, including glass, ceramics, metal, or suitable polymers. The insert part 2 may consist of a polymer of the following families: Polypropylene (PP), Polyethylene (PE), and copolymers; Ethylene Vinyl Acetate (EVA), Polyvinyl Chloride (PVC), silicone or generally any other polymer material which is known to the skilled person to be suitable for that purpose. If the insert part 2 comprises a protruding sealing lip, preferable materials for the insert part are thermoplastic elastomers, elastomers, and silicone, or any other suitable material that is comparably soft and elastic. The same applies to the sealing lip if it is made from another material than the body of the insert part 2. The insert part 2 may be manufactured by any suitable method, depending on the material used. If polymers are used, injection molding is the most preferable manufacturing method.

Since there is no material bonding between the insert part 2 and the wall sheets 101, 102 of the container 1, it is not necessary to choose compatible materials for the insert part and the adjacent layer of the wall, which provides more flexibility for the manufacturer when selecting the most appropriate materials.

The shape of the insert part 2 as shown in FIGS. 1(*a*), 1(*b*), 2(*a*) and 2(*b*) has the advantage that the insert part may be readily produced by injection molding, since there are no undercuts. The drain channel 22 in the form of the oblong depression ensures a continuing fluid connection between the access opening 121 and the storage compartment 11, even when the container 1 is completely drained. Even under the external force of a clamp element, e.g. clamp part 31 and/or clamp part 32 of a connection device 3 (FIG. 3), or due to the pressure difference between the inside and the outside of the container 1, the tubular connection formed by the drain channel 22 and the adjacent wall sheet 102 will not collapse.

Alternatively the drain channel 22 could be arranged on the upper surface 211 of the insert part 2, in which case no inner conduit would be necessary. However, such an embodiment would be detrimental to the sealing effect between the insert part 2 and the wall sheet 101 in the annular area around the access opening 121, since the relevant area would not be completely flat.

In the embodiment of the flexible container 1 depicted in FIG. 1(*b*), the wall sheets 101, 102 are essentially flat. Consequently also the insert part 2 must be as flat as possible, in order to avoid folding of the wall sheets 101, 102. In an alternative embodiment, one or both wall sheets 101, 102 may be provided with a hollow, in which the insert part 2 can be arranged. Such an embodiment has the advantage that more voluminous inserts can be used, which may for example contain additional features, such as a septum, or a bubble trap.

As an alternative to a completely flat surface of the insert part 2, the upper surface 211 facing the connection device 3 (FIG. 3) may also be convex, if the shape of the sealing and pressure elements of a connection device are adapted to that specific shape.

In another embodiment of the invention, the drain channel network of the surface of the insert part 2 is extended to the wall sheets 101, 102 of the flexible container 1. This can be achieved for example by hot embossing a grid of lines on at least a part of the inner surface of one or both wall sheets 101, 102. In such an embodiment the drain channel network of the insert part 2 is connected to the embossed grid line network. No portion of the content of the container 1 can be blocked and separated from the insert part 2 when the container collapses in a sub-optimal manner during emptying, even for very large containers or very flexible container wall sheets, since the liquid can always flow to the insert part 2 through the grid line network.

The possible geometrical form of a flexible container 1 according to an embodiment of the invention is not restricted to the essentially rectangular form as shown in FIG. 1(*a*), although a rectangular form is efficient and thus advantageous. The form of the flexible container 1 may be adapted to any specific need, particularly to the dimensions of a certain pump device. The same holds true for the form, position and dimensions of the storage compartment.

Figure 3:
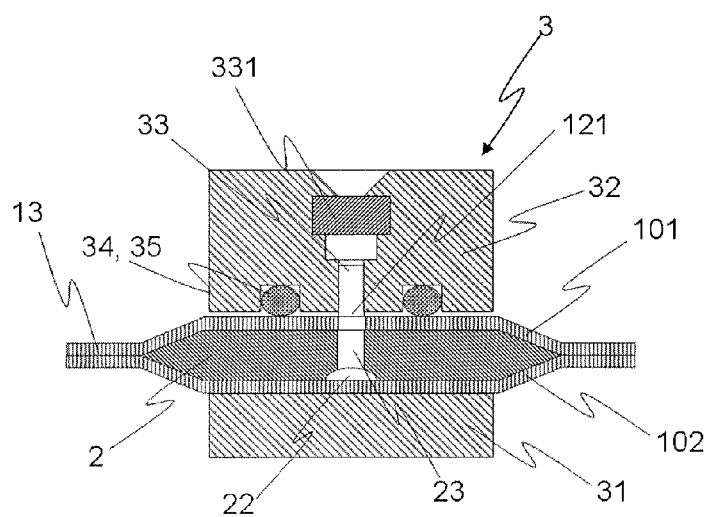
FIG. 3 schematically shows a flexible container according to the invention, interacting with a possible embodiment of a connection device, in a cross-section through the connection device, perpendicular to the longitudinal axis of the container.

The technical interaction between a flexible container 1 according to an embodiment of the invention and an infusion pump device is depicted in more detail in FIG. 3, which shows a flexible container 1 according to the invention, interacting with the connection device 3 of or for an infusion pump device (not shown), in a cross-section through the connection device 3 and the inner conduit of the insert part, perpendicular to a longitudinal axis 15 (FIG. 1(*a*)) of the container 1.

The shown connection device 3 comprises lower and upper clamp parts 31, 32, made from a stable, rigid material, such as metal or suitable polymer. The access area 12 of the flexible container 1 (FIG. 1(*a*)), with the insert part 2, is clamped between the two clamp parts 31, 32, the upper surface 211 of the insert part facing toward the upper clamp part 32. The upper clamp part 32 comprises a conduit system 33, connected to an infusion pump device (not shown), in which a septum 331 is arranged. The conduit system 33 is aligned with the access opening 121 and the inner conduit 23 of the insert part 2.

A sealing element 34 in the form of an 0-ring is arranged on the upper clamp part 32, facing toward the insert part 2 and pressed against the wall sheet 101. The sealing element 34 thus provides a circumferential sealing between the conduit system 33 of the connection device 3 and the access opening 121 of the flexible container.

After the necessary sealing has been established, the storage compartment 11 of the container 1 (FIG. 1(*a*)) is now fluidly connected to the conduit system 33 of the connection device, via the drain channel 22, the inner conduit 23, and the access opening 121. The conduit system 33 may be connected to an infusion pump device (not shown), via a separate conduit opening to the conduit system 33 or via a hollow needle arranged in the septum 331.

The septum 331 provided in the shown embodiment of a connection device 3 is only an optional feature and may be, for example made from silicon polymer. Through septum 331 a user may access the conduit system 33 and/or the container 1 with a syringe by penetrating the septum with a hollow needle. The user may, for example, fill or refill the container with a liquid medicament, originating from a larger container, or may clean the conduit system or deaerate the system.

After inserting the appropriate end, e.g., the access area 12, of the flexible container 1 between the two clamp parts 31, 32 of the connection device 3, the two clamp parts 31, 32 are locked together. A skilled person will know a number of different methods for friction-locking or form-locking said two parts. For example, one clamp part may be equipped with snap bolts, which are inserted into corresponding holes of the other clamp part. Said snap bolts could at the same time be used for positioning and/or fixating the container, for example if the container comprises corresponding holes 17 in a sealed area 14 of the wall sheets 101, 102 (see for example the embodiment of a container 1 according to the invention disclosed in FIG. 7(*c*)). In an advantageous embodiment the snap bolts are inserted into the holes 17 of the container 1, thereby fixing its position in a definite way in relation to the clamp parts 31, 32. European Patent Application 08170627 of the applicant discloses such a clamp locking system, which can also be applied for flexible containers according to this invention.

The connection device 3 may comprise further functional elements, such as for example a bubble trap, a pressure sensor, or a pressure transfer membrane for coupling a conduit system 33 of the connection device to a pressure sensor. Furthermore it may comprise a pumping/dosing mechanism, or part of a pumping mechanism, such as a micro membrane pump, or a micro plunger pump.

A connection device 3 according to an embodiment of the invention may be embodied as a separate unit, as shown in FIG. 3, or may be permanently attached to the flexible container 1, or may be directly attached to an infusion pump device. For example the lower clamp part 31 may be an integral part of a ground plate of an infusion pump device. The flexible container 1 itself may be easily removed from the infusion pump device, or may be an integral part of the device. In the former case a user, particularly a patient using the device, may replace an emptied container 1 with a new, pre-filled single-use container, or he may remove the container for refilling. Replaceable single-use containers are highly preferred for quality assurance reasons. In the latter case the container 1 is directly refilled in the device, for example by a septum 331 in the connection device 3 or by an additional port mounted on the container. If the container has to be replaced for maintenance reasons, this may be done by the user, or by a maintenance service.

Figure 4:
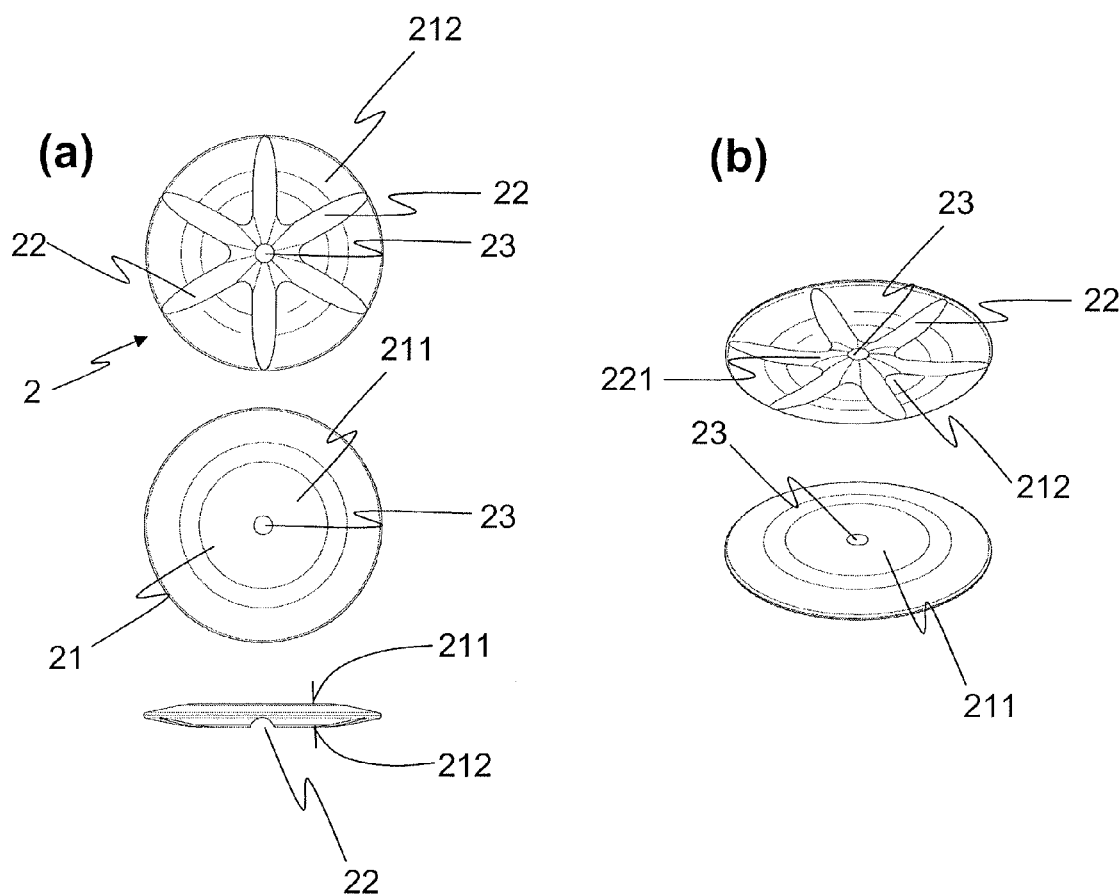
FIG. 4(a) schematically shows another embodiment of an insert part according to the invention, with a view of the lower and upper surfaces, and in a side view.
FIG. 4(b) schematically shows another embodiment of an insert part according to the invention, in a perspective view of the lower and upper surface of FIG. 4(a).

The insert part 2 of the flexible container disclosed in FIGS. 1(*a*), 1(*b*), 2(*a*) and 2(*b*) is designed to be positioned within the container 1 in one single, clearly defined orientation. Alternatively, however, it is possible to realize the insert part in a way that allows multiple orientations. Such an embodiment of an insert part 2 is depicted in FIGS. 4(*a*) and 4(*b*). Said insert part 2 has an essentially disc shaped form, with an inner conduit 23 arranged in the center of the disc. On one surface (e.g., surface 212) of the disc six drain channels 22 are symmetrically arranged, radiating from the inner conduit 23 towards the peripheral rim, and forming a drain channel network 221.

Rotation symmetric insert parts as shown in FIGS. 4(*a*) and 4(*b*) have the advantage that only the orientation of the two surfaces 211, 212 has to be correct. It is, however, irrelevant how the insert part 2 is rotationally oriented along its central axis. If the neck 16 of the flexible container 1 (FIG. 1(*a*)) is chosen sufficiently wide, in every orientation angle at least one drain channel 22 will open to the storage compartment 11, providing a fluid connection, e.g., via the drain channel 22 and inner conduit 23, between the access opening 121 and the storage compartment 11. This irrelevancy of the orientation angle significantly simplifies the assembly process of a flexible container 1 with an insert part 2.

Figure 5:
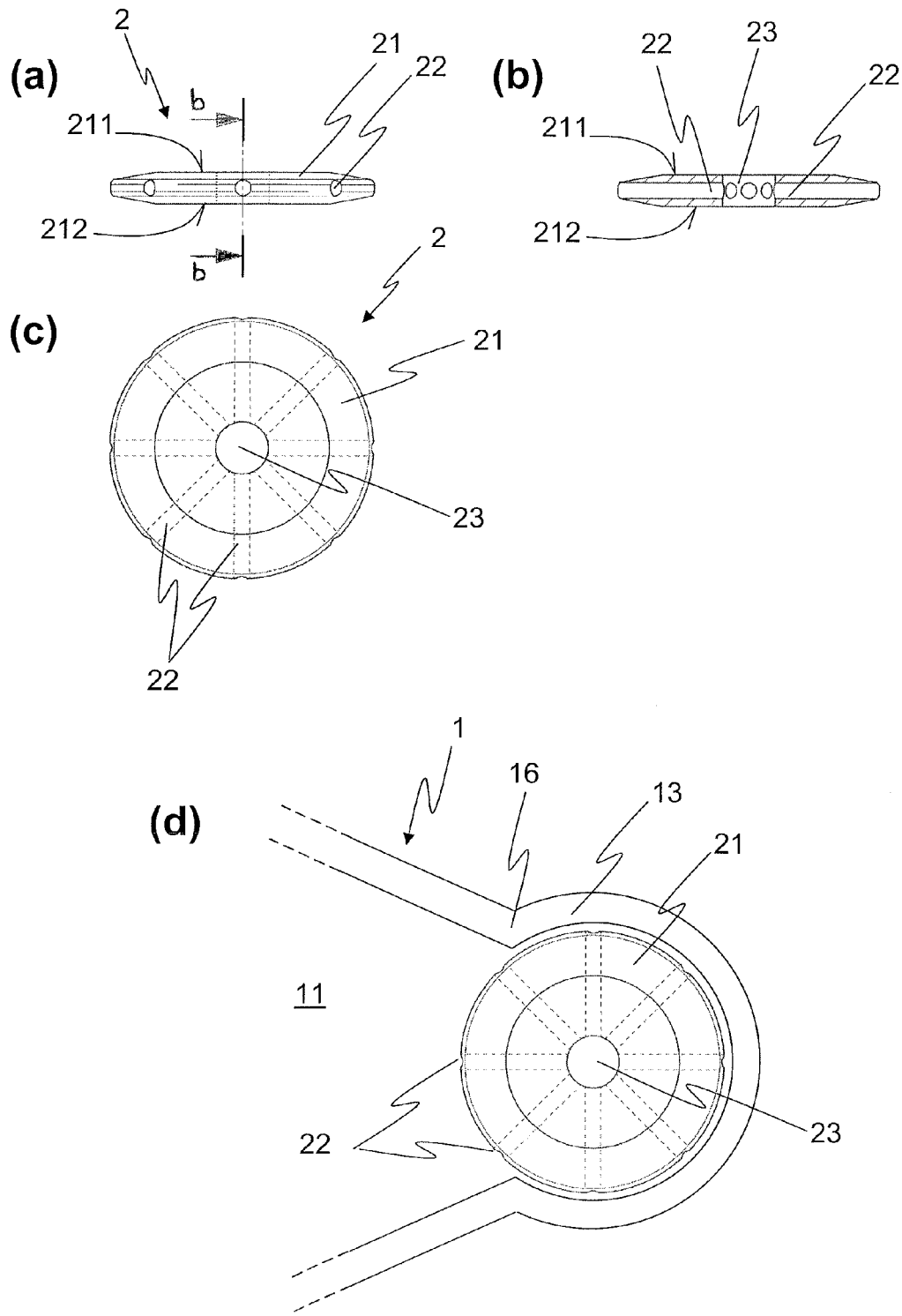

Yet another embodiment of an insert part 2 for use in a flexible container 1 according to an embodiment of the invention is shown in FIGS. 5(*a*)-5(*d*), where eight tubular drain channels 22 are radially arranged inside the body 21 of the insert part 2. The assembly of a flexible container 1 with such an insert part 2 is even simpler that with the insert part of FIG. 4, since both surfaces 211, 212 are equivalent. FIG. 5(*d*) depicts the access area of a flexible container 1 according to the invention, in which such an insert part is arranged with positive locking.

An additional advantage of an insert part 2 as shown in FIG. 5(*d*) is that also a possible dead volume in the peripheral zone between the sealing rim 13 and the edge of the insert part is accessible through the drain channels 22 facing toward the sealing rim 13. Furthermore there may be a circumferential channel around the flexible container between the two wall sheets close to the sealing rim 13, due to a certain stiffness of the wall sheets close to the sealing rim. It is thus possible to empty also said peripheral zone and circumferential channel, thereby further reducing the dead volume.

Figure 6:
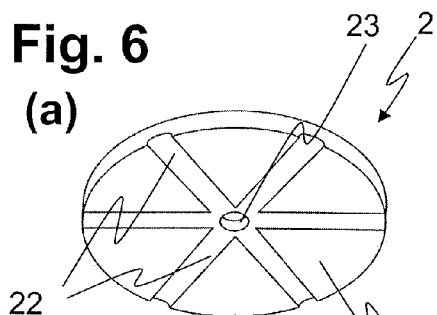
FIGS. 6(a), 6(b), 6(c) and 6(d) schematically show four different variants for drain channel arrangements of insert parts according to the invention, (a), (b) in a perspective view onto the lower surface, and (c), (d) with view onto the lower surface.
Figure 6:
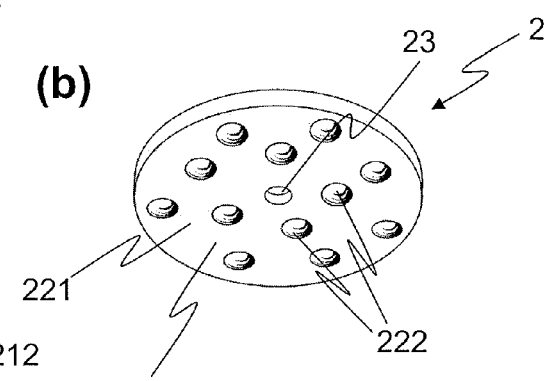
Figure 6:
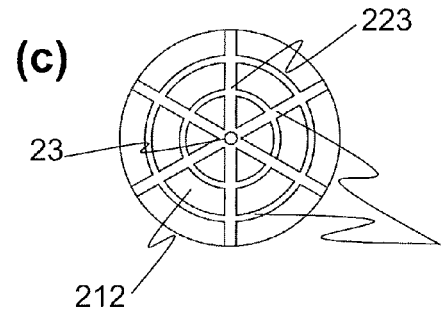
Figure 6:
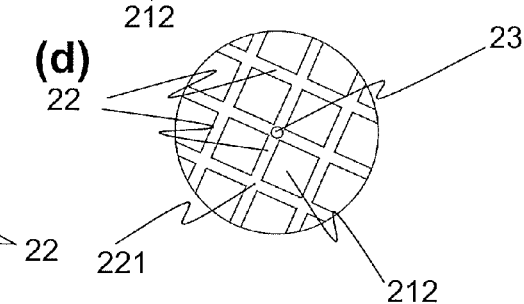

Other examples of possible arrangements of drain channels 22 of the various embodiments of the insert parts 2 are given in FIGS. 6(*a*)-6(*d*). FIG. 6(*a*) shows another embodiment of an insert part 2, with three drain channels 22 arranged in a star-like manner on the lower surface 212 of the insert part 2. In the variant in FIG. 6(*b*) a number of protrusions 222 are arranged on the lower surface 212 of the insert part 2, the interstice between said protrusions forming a network 221 of drain channels 22. In the embodiment in FIG. 6(*c*) three linear and two circular drain channels 22 are arranged on the surface 212, while in FIG. 6(*d*) the drain channels 22 form a grid-like network 221.

Generally the drain channels 22 should be as shallow as possible, in order to decrease the dead volume. Among other factors, the achievable minimum depth of the drain channels 22 of a given channel network 221 in order to avoid blocking of the channels depends on the flexibility of the material of the wall sheet 102 and the width of the channels 22. Furthermore a given minimum flow must be ensured, which depends for example on the demands of the dosing pump and the viscosity of the liquid medicament.

Figure 7:
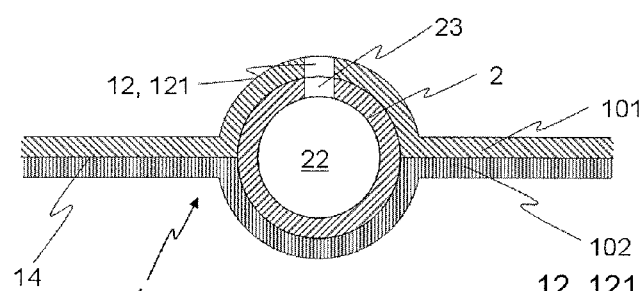
FIGS. 7(a), 7(b) and 7(c) schematically show another variant of a flexible container according to the invention, with a tubular element as an insert part, in a cross-section perpendicular to the axis of the tubular element, in a cross-section along the axis of the tubular element, and in a top view, respectively.
Figure 7:
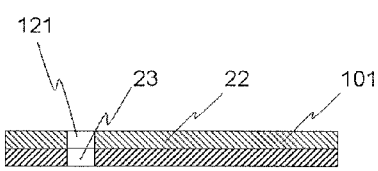
Figure 7:
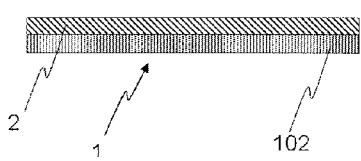
Figure 7:
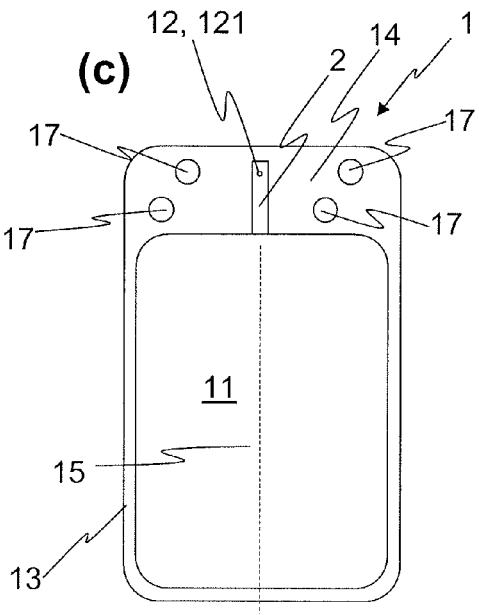

Another advantageous variant of a flexible container 1 according to the invention is shown in FIGS. 7(*a*), 7(*b*) and 7(*c*). In this particular embodiment the insert part 2 is realized as a tubular element arranged in the access area 12 of the flexible container 1, parallel to the longitudinal axis 15 (FIG. 7(*c*)). The access opening 121 is arranged on top of the tubular insert part 2. One open end of the tubular insert part 2 opens to the storage compartment 11, while the other end is blocked by the sealing rim 13. The drain channel 22 and inner conduit 23 of the tubular insert part 2 are both provided by the inner space of the tubular element. The sealing element and pressure element of a connection device have to be adapted to the specific form non-flat form of the surface of the wall sheet around the access opening 121.

One of the features of such an embodiment of a flexible container 1 is that a very simple insert part 2 may be used, which may even be provided continuously during manufacture, for example, feed from a bobbin. In an alternative version the tubular insert part 2 may even protrude into the storage volume compartment 11 of the container 1. In another variant the tubular insert part 2 may be bent to a half circle, with both ends facing toward the storage compartment 11. The access opening 121 would then be positioned in the middle of the tubular insert part 2.

In the embodiment of the flexible container 1 disclosed in FIG. 7(*c*), the sealing rim 13 is broadened in the access area 12, and forms a sealed area 14. In said sealed area 14 four holes 17 are arranged, which act as positioning elements for precisely positioning the flexible container 1 within a connection device. For example, the connection device may comprise positioning bolts that interact with the positioning holes 17. In another possible variant the positioning elements may be grooves or protrusions in the sealed area 14 that interact with protrusions and/or grooves arranged on clamp parts of the connection device. The use of positioning elements is also favorable in the context of all other embodiments of flexible containers according to the invention, with other types of insert parts. In another variant embodiment, as it is realized in FIG. 7(*c*), the positioning elements 17 are arranged asymmetrically. This will allow only one possible way to connect the container 1 with a connection device, which reduces the risk of wrong manipulations by a user.

When puncturing the access opening 121 of a flexible container 1 according to the invention, care must be taken not to accidentally puncture both wall sheets 101, 102, which would compromise the sealing of the connection between the container and the connection device. This can be achieved by an optional needle stop 24 arranged in the insert part 2, as shown in FIGS. 8(b) and 9.

Figure 8:
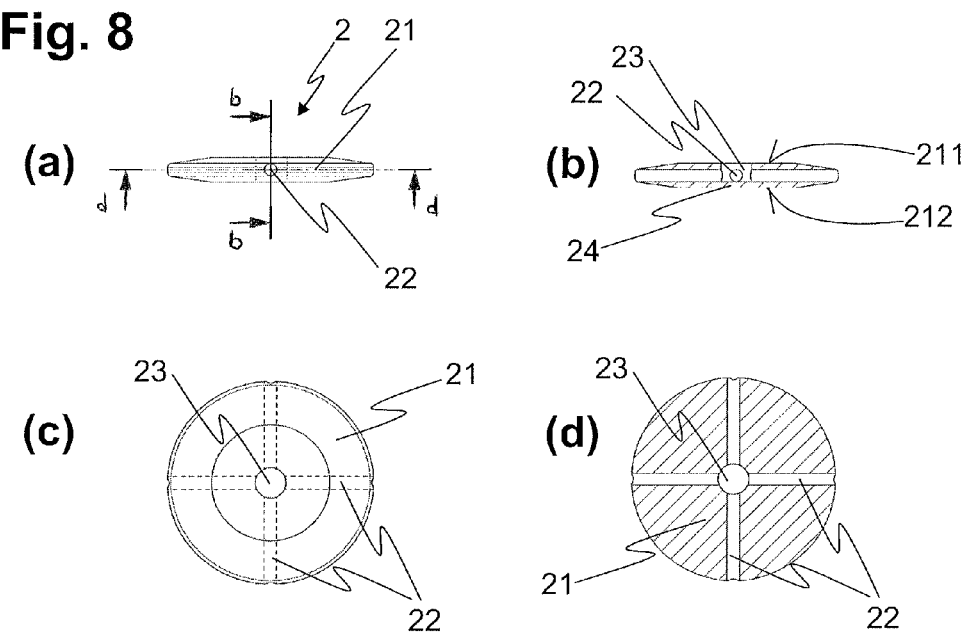
FIGS. 8(a), 8(b), 8(c) and 8(d) schematically show an embodiment of an insert part according to the invention with a needle stop, in a side view, in a cross-section through plane b-b, in a top view, and in a cross-section through plane d-d, respectively.
Figure 9:
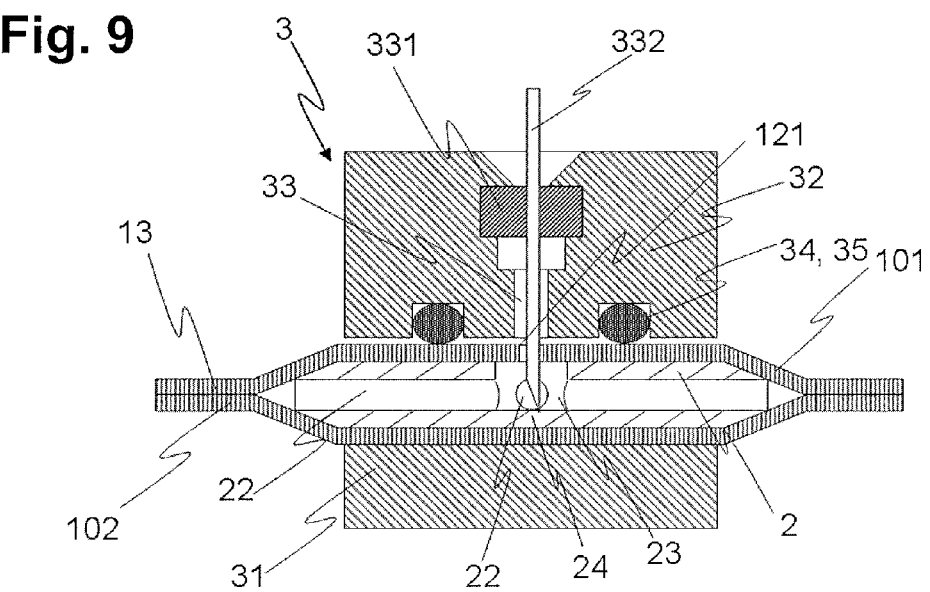
FIG. 9 schematically shows a flexible container according to the invention, interacting with a possible embodiment of a connection device, with an insert part comprising a needle stop, in a cross-section through the connection device, perpendicular to the longitudinal axis of the container.

In the insert parts 2 shown in FIGS. 8(b), 8(c), 8(d) and 9, the inner conduit 23 is realized as a blind hole, the remaining rigid wall of the surface 212 opposite to the connection device 3 acting as a needle stop 24. When a needle 332 is pushed through the septum 331 and the upper wall sheet 101, the needle stop 24 prevents the point of the needle 332 from reaching the other wall sheet 102. A needle stopper 24 as shown in FIGS. 8(b) and 9 may not only be used in an insert part with tubular drain channels 22, but also with drain channels realized as oblong depressions as depicted, for example, in FIGS. 2(a), 2(b), 3, 4(a) and 4(b).

In the embodiments of flexible containers 1 discussed so far, the insert part 2 is immobilized within the container by positively locking it within a compartment divided from the storage compartment 11 by a constriction or neck 16 (FIG. 1(a)). However, a flexible container 1 according to an embodiment of the invention may also comprise only one single compartment, acting both as the storage compartment 11 and as the access area 12. Two possible examples of such flexible containers according to the invention are shown in FIGS. 10(a) and 10(b).

Figure 10:
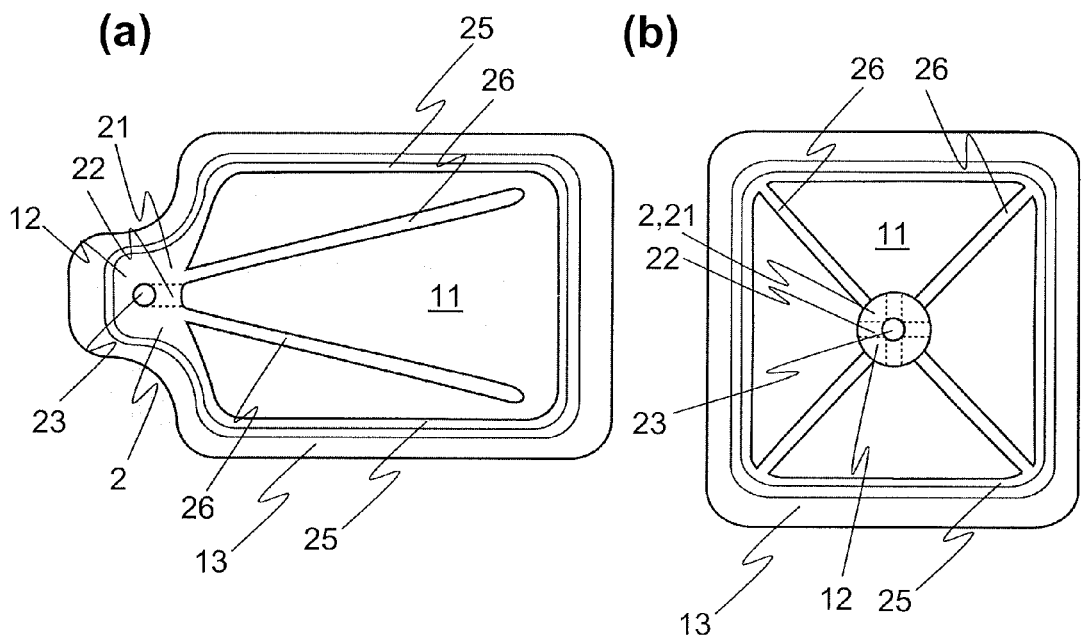
FIGS. 10(a) and 10(b) schematically show in a top view two embodiments of a flexible container according to the invention, in which the container comprises one single compartment.
Figure 11:
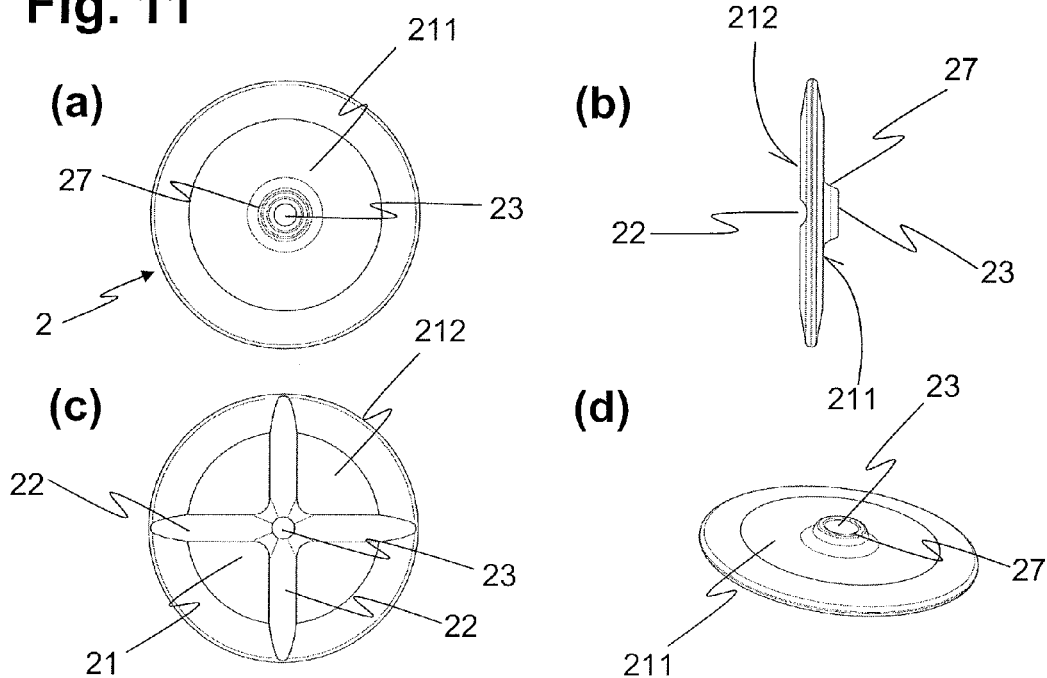
FIGS. 11(a), 11(b), 11(c) and 11(d) schematically show an embodiment of an insert part according to the invention, comprising a sealing lip, in a top view, in a side view, in a bottom view, and in a perspective view, respectively.

In the embodiment shown in FIG. 10(a), the inner compartment of the access area 12 comprises a bulge at its periphery, in which the body 21 of the insert part 2 is arranged. Since the bulge is not undercut, the previously discussed insert parts 2 would not be positively locked within the access area 12 due to the bulge. For that purpose the insert part 2 in FIG. 10(a) comprises a hoop-like positioning element 25, which is located inside the storage compartment 11 along the sealing rim 13, thereby positively locking the insert part 2 within the container 1. In addition the disclosed insert part 2 comprises optional two distance elements 26, protruding into the storage compartment 11. When the flexible container 1 is nearly completely drained, the distance elements 26 will prevent a constriction of a part of the storage compartment 11. On the other hand, if the container 1 is provided initially empty, the distance elements 26 will prevent the wall sheets 101, 102 from sticking together.

FIG. 10(b) depicts a flexible container according to another embodiment of the invention, in which the insert part 2 is arranged in the center of a rectangularly shaped storage compartment 11. Again the insert part 2 is kept in position by a hoop-like positioning element 25, which is attached to the insert part 2 by four radial distance elements 26. In this variant the access area 12 is located in the center of the storage compartment 11.

A further variant of an insert part 2 for use with a flexible container 1 according to an embodiment of the invention is shown in FIGS. 11(a), 11(b), 11(c), 11(d), 12(a), 12(b) and 12(c). In the depicted insert part 2, which has four oblong depressions as drain channels 22, a circular sealing lip 27 is arranged around the access opening 121. The sealing lip 27 protrudes from the essentially flat upper surface 211 of the insert part 2. In a flexible container with such an insert part, the access opening 121 on the upper wall sheet 101 comprises a larger circular hole 103, through which the sealing lip 27 protrudes. The sealing lip 27 is designed to interact with the sealing element 34 of a connection device 3, thereby providing a liquid-tight sealing between the conduit system 33 of the connection device and the inner conduit 23 of the insert part. A liquid-tight sealing between the wall sheet 101 and the insert part 2 is the result of the external pressure of a pressure element 35 of the connection device 3, acting on an annular area around the access opening 121 and the sealing lip 27.

To ensure sterility, the access opening or even the whole access area may initially be covered by a removable cap or coverage. In a preferred embodiment of a flexible container, with a readily attached connection device, such removable caps or covers will typically be provided on the fluid connectors of the connection device.

One noted feature of such an embodiment of an insert part and a flexible container is the fact that the liquid medicament inside the container will only get into contact with the inner surface of the wall sheets. This may be especially advantageous if the wall sheet has a multiple layer structure, and a contact between the liquid medicament and one of the outer layers should be avoided.

Figure 12:
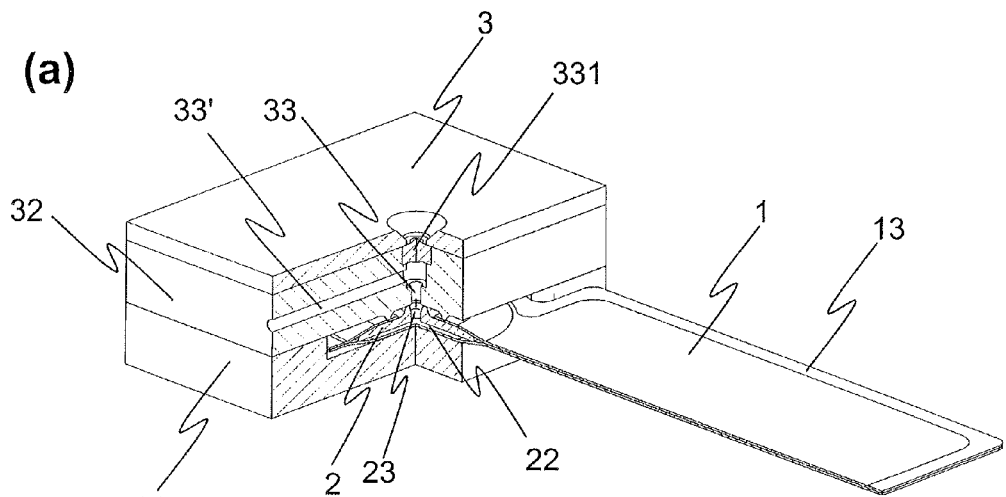
FIGS. 12(a), 12(b) and 12(c) schematically show a flexible container according to the invention, with an insert part as shown in FIG. 11, with the flexible container completely drained (FIG. 12(a)), with the container filled (FIG. 12(b)), and in a cross-section through the connection device, perpendicular to the longitudinal axis of the container (FIG. 12(c)).
Figure 12:
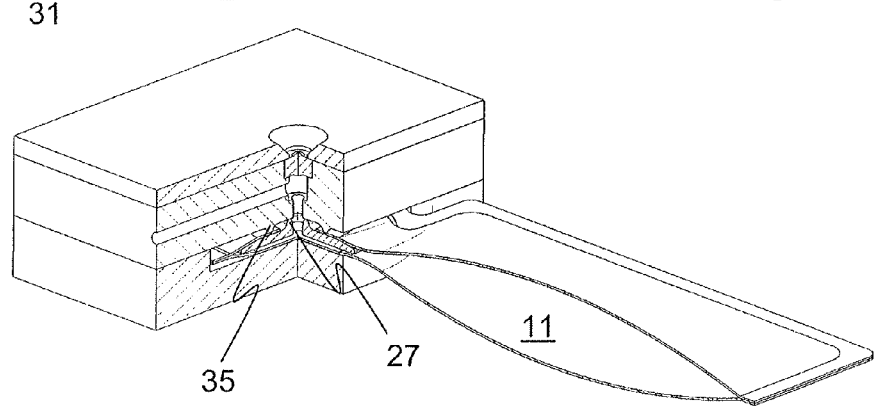
Figure 12:
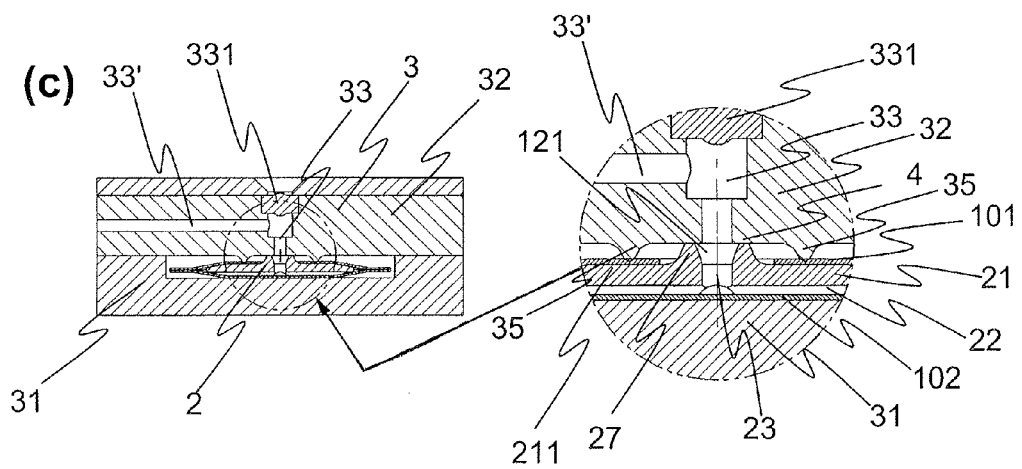
Figure 13:
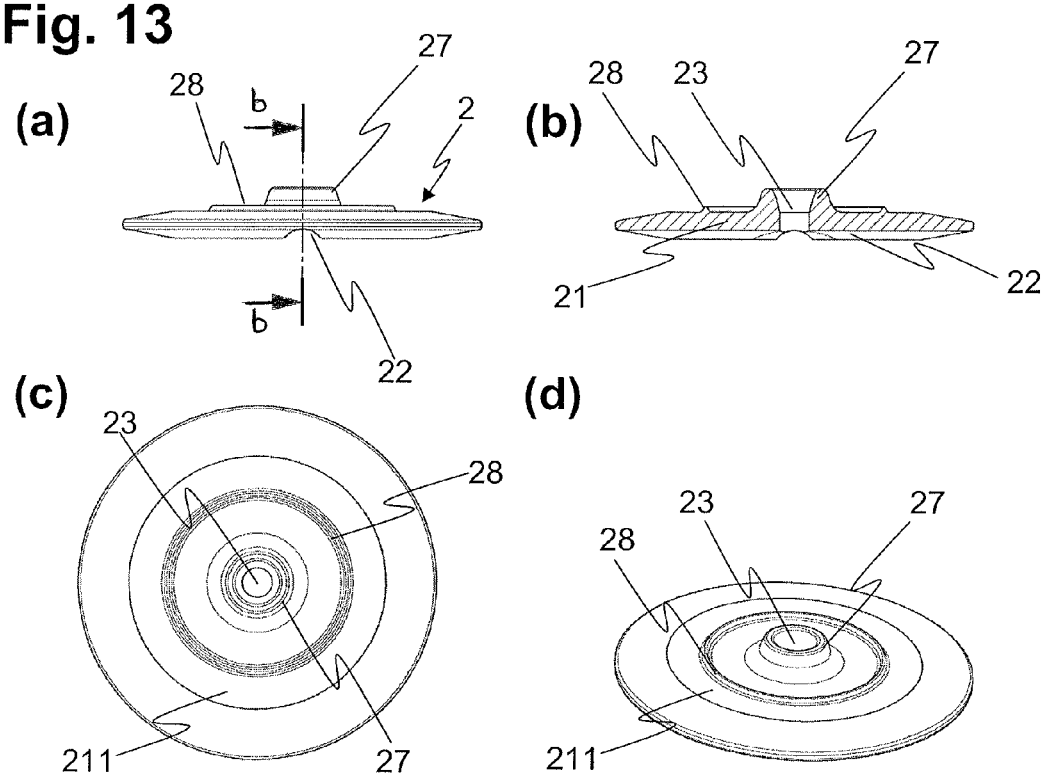
FIGS. 13(a), 13(b), 13(c) and 13(d) schematically show an embodiment of an insert part according to the invention, comprising a primary and a secondary sealing lip, in a side view, in a cross-section through plane b-b, in a top view, and in a perspective view, respectively.
Figure 14:
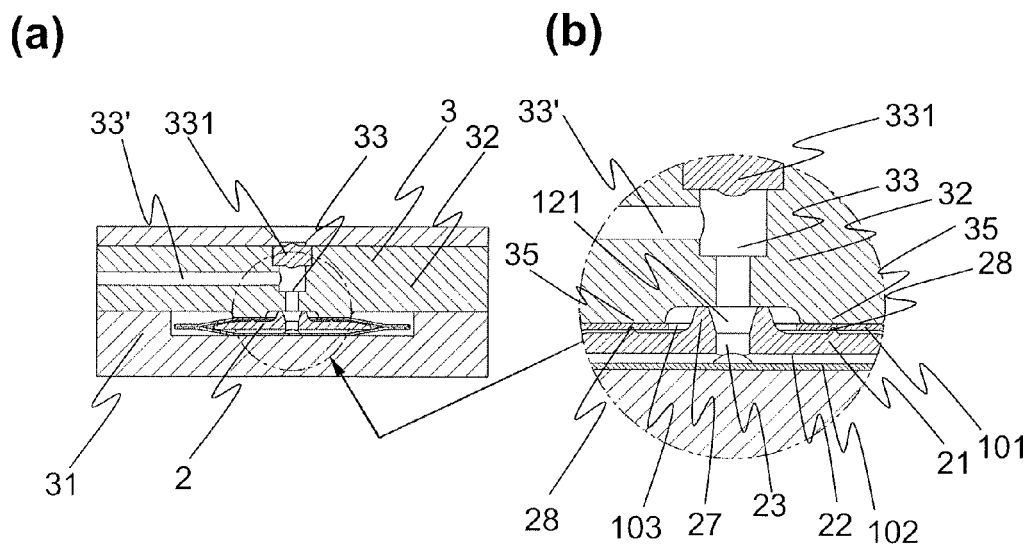
FIGS. 14(a) and 14(b) schematically show a flexible container according to the invention with an insert part as disclosed in FIG. 13, interacting with a possible embodiment of a connection device, each in a cross-section through the connection device, perpendicular to the longitudinal axis of the container.
Figure 15:
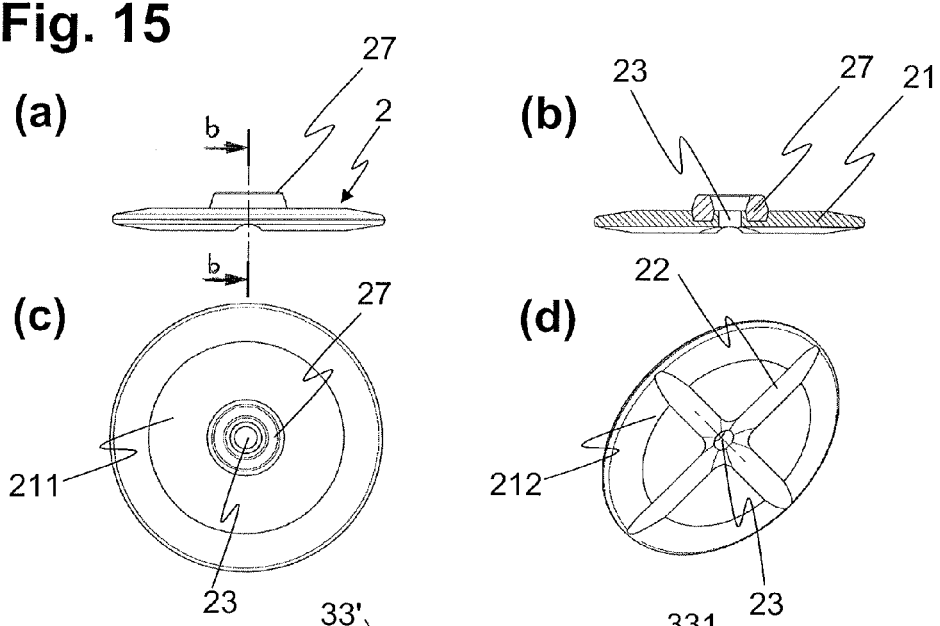
FIGS. 15(a), 15(b), 15(c) and 15(d) schematically show yet another embodiment of an insert part according to the invention, with a sealing lip made of a more elastic material, in a side view, in a cross-section through plane b-b, in a top view, and in a perspective view onto the lower surface, respectively.

The use of a flexible container 1 according to an embodiment of the invention with an insert part 2 as shown in FIGS. 11(a)-11(d) is explained in more detail in FIGS. 12(a)-12(c). An initially empty container 1 is fastened in a connection device 3 (FIG. 12(a)). Said connection device comprises a lower clamp part 31 with a recess, in which the access area 12 of the container is located, and an upper clamp part 32. The upper clamp part 32 comprises a pressure element 35 in the form of a circular lip, pressing together the surface 211 of the insert part 2 and the upper wall sheet 101. The sealing lip 27 is in close contact with the surface of the upper clamp part 32, providing a fluid connection between the inner conduit 23 and the conduit system 33. In the shown embodiment the upper clamp part 32 does not comprise a special sealing element, but a flat contact zone 4. This is, for example, possible if the polymer material of the insert part 2 and/or the clamp part itself shows a certain degree of elasticity. If the combined elasticity of sealing lip 27 and sealing element 34 is not sufficient, a sealing ring may be arranged on the clamp part 32.

After the container 1 has been fluidly connected with the connection device 3, it is filled with its liquid content using a syringe with hollow needle, through the septum 331. When the container 1 is completely filled, the hollow needle is retracted and the system comprising the container 1 and the connection device 3 are ready for use (FIG. 12(b)). A pump device (not shown) may now suck liquid from the container 1 through the conduit system 33, 33'. The septum 331 may also be used to deaerate the conduit system.

A further variant of an insert part 2 similar to FIGS. 11(a)-11(d) is given in FIGS. 13(a), 13(b), 13(c), 13(d), 14(a) and 14(b). In said embodiment the upper surface 211 of the insert part 2 comprises a secondary, outer sealing lip 28, arranged in the periphery of the first, central sealing lip 27. When interacting with a flatly surfaced pressure element 35 of a connection device 3 (FIG. 14(b)), the secondary sealing lip 28 increases the local pressure between the upper surface 211 of the insert part 2 and the adjacent wall sheet 101, improving the sealing between insert part 2 and wall sheet 101.

Figure 16:
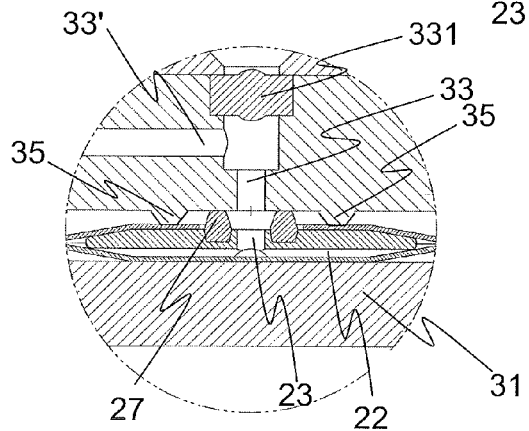
FIG. 16 schematically shows a flexible container according to the invention with an insert part as disclosed in FIG. 15, interacting with a possible embodiment of a connection device, in a cross-section through the connection device, perpendicular to the longitudinal axis of the container.

FIGS. 15(a)-15(d) disclose an embodiment of an insert part 2 with a sealing 27, manufactured by two-component injection molding. While the body 21 of the insert part 2 consists of a rigid material, the sealing lip 27 is made from a comparably soft, elastomeric material. When locked in a connection device 3 (FIG. 16), the resilient elastomeric sealing lip 27 establishes the liquid-tight connection of the access opening 121 with the conduit system 33 of the upper clamp part 32.

In all embodiments of flexible containers according to the invention discussed so far, the insert part 2 and the adjacent wall sheet 101 were not bounded to each other. When a liquid-tight sealing between insert part 2 and wall sheet 101 is necessary, as for example in the embodiments shown in FIGS. 11(a)-11(d), 12(a)-12(c), 13(a)-13(d), and 14(a)-14(b), said sealing is provided solely by the temporarily exerted external pressure force 35 acting on the two elements 211, 101. Alternatively, in all disclosed embodiments the insert part may be permanently connected to the wall sheet, by heat sealing, ultrasonic welding, high-frequency inductive welding, gluing, or any other suitable method. On one hand, this variant of the invention needs an additional step during manufacture, but on the other hand there is no need for a pressure element on the clamp part of a connection device 3.

Figure 17:
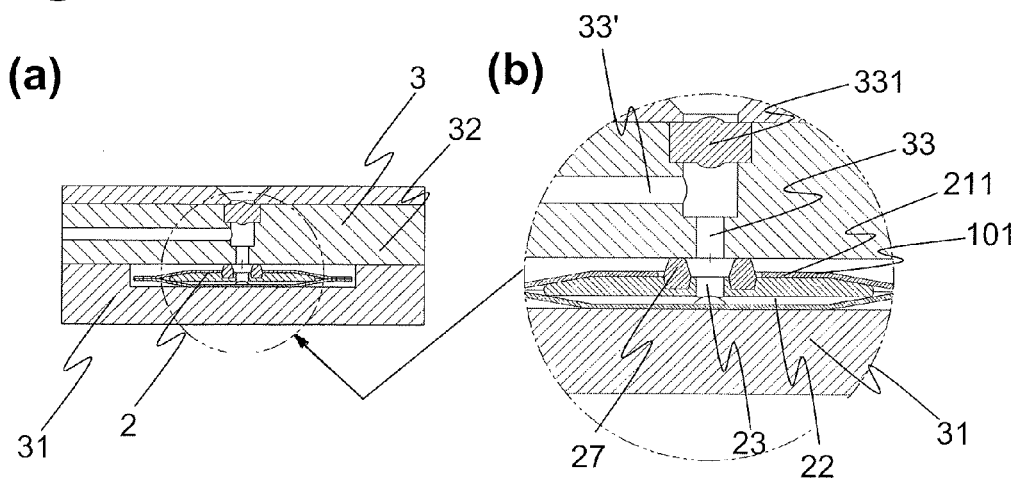
FIGS. 17(a) and 17(b) schematically show another flexible container according to the invention with an insert part as disclosed in FIG. 15, permanently sealed to the adjacent wall sheet, interacting with a possible embodiment of a connection device, each in a cross-section through the connection device, perpendicular to the longitudinal axis of the container.

An example of a flexible container 1 according to another embodiment of the invention with permanently sealed wall sheet 101 and insert part 2 is shown in FIGS. 17(*a*) and 17(*b*). The disclosed insert part 2 is similar to the one shown in FIGS. 14(*a*)-14(*b*). However, since the surface 211 of the insert part 2 is sealed to the wall sheet 101, there is no need for an additional pressure element of the connection element.

The present invention is not to be limited in scope by the specific embodiments described herein. Indeed, various modifications of the present invention, in addition to those described herein, will be apparent to those skilled in the art from the foregoing description and accompanying drawings. Thus, such modifications are intended to fall within the scope of the appended claims. Additionally, various references are cited throughout the specification, the disclosures of which are each incorporated herein by reference in their entirety.

What is claimed is:

1. A flexible container for storing a liquid medicament and connection to an outer conduit system, said flexible container comprising:
    a container wall consisting of two adjacent wall sheets of flexible material that are sealed together along a sealing rim;
    a storage compartment for the liquid medicament;
    an access opening comprises a hole arranged in one of the wall sheets, wherein the storage compartment and the access opening are in fluid connection, and the access opening is designed to be fluidly connected to the outer conduit system; and
    an insert part that is provided entirely within the container and immobilized only by positive locking between the two adjacent wall sheets and the sealing rim of the wall sheets, and that defines an interior conduit system which fluidly connects the storage compartment and the hole of the access opening, said insert part having an essentially flat body that has an upper surface defining an opening to the interior conduit system, and wherein the hole of the access opening is arranged directly above the opening of the interior conduit system of the insert part.

2. The flexible container according to claim 1, wherein the insert part is arranged and positively locked in an access area of the container, which is separated from the storage compartment by a neck or constriction.

3. The flexible container according to claim 1, further comprising elements for at least one of positioning and fixating the flexible container in a connection device.

4. The flexible container according to claim 3, wherein the connection device is of an infusion pump device.

5. The flexible container according to claim 3, wherein the elements for at least one of positioning and fixating are two or more holes or grooves arranged in a sealed area of the container or in an area of the wall sheets outside of the sealed area that does not belong to the storage compartment.

6. The flexible container according to claim 1, further comprising a connection device for use in an infusion pump device, and which comprises two clamp parts that are adapted to at least one of positively and non-positively lock the flexible container, and to fluidly connect an access opening of the flexible container to a conduit system of the connection device.

7. The flexible container according to claim 6, wherein one of the clamp parts faces towards the access opening and comprises a sealing element that is adapted to fluidly connecting the conduit system of the connection device with the access opening of the flexible container.

8. The flexible container according to claim 6, wherein a surface of the clamp parts of the connection device is adapted to an exterior shape of the flexible container.

9. The flexible container according to claim 8, wherein the exterior shape is an access area of the container.

10. The flexible container according to claim 3, wherein the connection device comprises elements for at least one of positioning and fixating the flexible container which interact with the elements for at least one of positioning and fixating of the flexible container.

11. The flexible container according to claim 1 wherein the interior conduit system of the insert part has one or more drain channels that lead to an outer edge of the body, and an inner conduit opening toward the upper surface that leads to the access opening, and being fluidly connected to the one or more drain channels that lead to the outer edge of the body.

12. The flexible container according to claim 11 wherein the one or more drain channels are embodied as at least one of depressions arranged on a lower surface of the insert part, and tubular conduits arranged inside the body of the insert part.

13. The flexible container according to claim 11 further comprising one or more positioning elements adapted to positively locking the insert part in the flexible container.

14. A device for the automated release of a liquid medicament comprising at least one flexible container according to claim 1.

* * * * *